(12) United States Patent
Bonaguidi et al.

(10) Patent No.: US 7,775,376 B2
(45) Date of Patent: Aug. 17, 2010

(54) FILTER FOR THE SEPARATION OF LEUKOCYTES FROM WHOLE BLOOD OR BLOOD PREPARATIONS, METHOD FOR PRODUCTION OF SAID FILTER, CORRESPONDING DEVICE AND USE THEREOF

(75) Inventors: Paolo Bonaguidi, Pisa (IT); Giorgio Mari, Mirandola (IT); Paolo Verri, Concordia (IT)

(73) Assignee: Fresenius Hemocare Italia S.R.L., Cavezzo (Modena) (IT)

( * ) Notice: Subject to any disclaimer, the term of this patent is extended or adjusted under 35 U.S.C. 154(b) by 698 days.

(21) Appl. No.: 10/543,444

(22) PCT Filed: Jan. 22, 2004

(86) PCT No.: PCT/EP2004/000489

§ 371 (c)(1),
(2), (4) Date: Apr. 11, 2006

(87) PCT Pub. No.: WO2004/064980

PCT Pub. Date: Aug. 5, 2004

(65) Prior Publication Data

US 2006/0207937 A1    Sep. 21, 2006

(30) Foreign Application Priority Data

Jan. 24, 2003    (IT) .......................... TO2003A0039

(51) Int. Cl.
  *B01D 29/00* (2006.01)
  *B01D 35/00* (2006.01)
  *B01D 39/00* (2006.01)
  *B01D 39/16* (2006.01)

(52) U.S. Cl. .................. 210/504; 210/348; 210/490; 210/500.27; 210/500.42; 210/503; 210/505; 210/506; 210/507

(58) Field of Classification Search .............. 210/323.1, 210/348, 500.27, 500.36, 500.42, 503, 504, 210/505, 506, 490, 507, 508
See application file for complete search history.

(56) References Cited

U.S. PATENT DOCUMENTS

| 4,880,548 | A |   | 11/1989 | Pall et al. |
| 4,929,510 | A | * | 5/1990 | Ruckenstein et al. ........ 428/520 |
| 4,976,861 | A | * | 12/1990 | Pall ............................ 210/508 |
| 5,162,102 | A |   | 11/1992 | Nogawa et al. |
| 5,445,736 | A |   | 8/1995 | Pall et al. |
| 5,478,470 | A | * | 12/1995 | Fukuda et al. ........... 210/500.1 |
| 5,580,465 | A |   | 12/1996 | Pall et al. |
| 5,895,575 | A |   | 4/1999 | Kraus et al. |
| 6,358,557 | B1 | * | 3/2002 | Wang et al. ................ 427/2.24 |
| 6,437,040 | B2 | * | 8/2002 | Anthony et al. ............. 524/505 |
| 6,841,639 | B1 | * | 1/2005 | Redman et al. ............. 526/277 |
| 2004/0082494 | A1 | * | 4/2004 | Queval et al. ............... 510/475 |
| 2006/0169635 | A1 | * | 8/2006 | Zambianchi et al. ... 210/500.36 |
| 2006/0180542 | A1 | * | 8/2006 | Mari et al. .................. 210/489 |

FOREIGN PATENT DOCUMENTS

| JP | 7025776 A | 1/1995 |
| JP | 10-33668 A | 2/1998 |
| JP | 2001-137337 A | 5/2001 |

OTHER PUBLICATIONS

Japanese Office Action, Apr. 22, 2009, JP Application No. 2006-500005.
Brief English Summary of JP 7025776, (1995).

* cited by examiner

*Primary Examiner*—John Kim
(74) *Attorney, Agent, or Firm*—Occhiuti Rohlicek & Tsao LLP

(57) ABSTRACT

The invention relates to a filter for the separation of leukocytes from whole blood, comprising a hydrophobic support material and a polymeric coating material, whereby the surface of the filter has a critical surface wetting tension in the range 50 to 80 dyn/cm and the polymeric coating material may be obtained by polymerisation reaction of mixtures comprising hydrophobic and hydrophilic monomers. The invention further relates to a method for production of said filter and devices for the separation of leukocytes from whole blood and the use of the filter.

16 Claims, No Drawings

FILTER FOR THE SEPARATION OF LEUKOCYTES FROM WHOLE BLOOD OR BLOOD PREPARATIONS, METHOD FOR PRODUCTION OF SAID FILTER, CORRESPONDING DEVICE AND USE THEREOF

FIELD OF INVENTION

The present invention relates to filters for the separation of leukocytes from whole blood and/or blood preparations, a method for producing said filter and devices which contain these filters. Furthermore, the invention relates to the use of these filters for the separation of leukocytes from whole blood and/or blood preparations.

BACKGROUND OF THE INVENTION

For treating patients with certain diseases use is made of concentrates of blood components which are administered to the patients. The blood component concentrates may be obtained by subjecting whole blood to density centrifuging. They should exhibit the lowest possible concentration of leukocytes because they may trigger immune reactions in the patient. For this reason an attempt is made to remove leukocytes from blood preparations.

Filters for separating leukocytes from blood preparations are known in the art. For example, the patents U.S. Pat. No. 4,880,548, U.S. Pat. No. 5,445,736 and U.S. Pat. No. 5,580,465 describe filters which are able to separate leukocytes (WBC) from concentrates of blood platelets (PLT). However, such filters are not suitable for separating leukocytes from whole blood because the erythrocytes (RC) are modified on contact with the filter material.

The separation of leukocytes from whole blood is described in U.S. Pat. No. 5,895,575. The filter material incorporates a hydrophobic support material, for example a fibre non-woven fabric of polyethylene terephthalate, to which a hydrophilic polysaccharide soluble in water is applied. The problem here is the relatively low separation of the leukocytes from whole blood. Compared to the filters described in U.S. Pat. No. 4,880,548, the filters coated with the polysaccharides separate far fewer leukocytes from the blood preparation. Although this separation can be improved by means of nitrocellulose filters, such systems are expensive to purchase and use. Moreover, the water solubility of the coating material is a problem. Since whole blood contains large quantities of water, the coating material may be washed out. As a result of this, however, thrombocytes or platulocytes are retained on the filter material. The particular problem here is that this loss takes place continuously. Although a cross-linking reaction intended to reduce the solubility is described in U.S. Pat. No. 5,895,575, such cross-linking causes further problems. In particular, residues of the cross-linking agent may reach the blood circulation. Furthermore, very intense cross-linking may result in reduced permeability of the filter. Too little cross-linking, however, may not prevent wash-out completely.

SUMMARY OF THE INVENTION

One object of the invention consists in providing filters for the separation of leukocytes from whole blood and/or blood preparations which, although they retain leukocytes extremely efficiently, allow blood platelets and erythrocytes to pass through with as few obstructions as possible.

A further object of the invention consists in providing filters which exhibit considerable durability. In particular, the filters should retain their permeability to blood platelets even after prolonged use.

A further object of the invention is to make filters available which are simple and inexpensive to produce. In particular, it should be possible to clean the materials used without problem in order to meet the medical requirements.

These objects and other objects which, although not mentioned specifically but which may be derived from the contexts discussed here or may necessarily result from them, are achieved in accordance with the present invention.

Because the surface of filters which exhibit a hydrophobic support material and a polymeric coating material also exhibit a critical surface wetting tension ranging from 50 to 80 dyn/cm, wherein the polymeric coating material may be obtained by a polyreaction of mixtures which contain hydrophobic and hydrophilic monomers, it is possible to make available filters for separating leukocytes from whole blood which exhibit an extremely high leukocyte retention capacity.

The following advantages in particular are achieved as a result of the inventive measures taken:

The filters according to the invention exhibit a high permeability to blood platelets and erythrocytes.

The filters according to the invention exhibit long durability, where the permeability to blood platelets in particular remains very high in prolonged use. Here, the filters according to the invention exhibit a very low wash-out.

The filters can be produced inexpensively and the materials used can be cleaned easily, thereby meeting the medical requirements.

The filters exhibit excellent conductivity. For instance, the filters according to the invention are characterised by a high separation of leukocytes, with extremely high permeability to and low retention capacity for blood platelets. Furthermore, the filters according to the invention can be operated at relatively high flow rates. In addition, relatively little material is required for the filter materials to achieve a certain filter efficiency.

DETAILED DESCRIPTION

The filters according to the invention exhibit a hydrophobic support material. Such materials are known to the expert and include, in particular, flat structures such as membranes and fibre non-woven fabrics that are able to separate particles because of size differences. The term hydrophobic means that the support material is insoluble in water, the solubility in water being less than or equal to 0.1 g/l at 20° C.

The membranes may be produced from, among other things, polycarbonates, acryl polymers, polyvinyl chlorides, polyamides and nitrocellulose. The pore size of these membranes preferably ranges from 2 to 20 µm without this resulting in any limitation.

Ideal fibre non-woven fabrics may be obtained from, among other things, polyester, cellulose, polyamides and polypropylenes. Of these materials polyesters are particularly preferred, e.g. polyethylene terephthalate (PET), polybutylene terephthalate (PBT) and polytrimethylene terephthalate (PTT). Such non-woven fabrics are preferably produced from fibres which exhibit a diameter ranging from 0.5 to 8 µm, particularly 1 to 4 µm, and more particularly 1.8 to 3 µm. In this case, particular preference is given to crystalline fibres whose crystallinity is at least 50%, and in particular at least 80%. This value can be measured by X-ray diffraction.

The surface density of the fibre non-woven fabrics generally ranges from 10 to 200 g/m², and preferably from 15 to 100 g/m², and more preferably from 20 to 60 g/m², without this resulting in any limitation. The surface density may, for example, be determined according to ISO 9073-1:1989 and EDANA ERT 40.9-90. The thickness of the non-woven fabric, may lie within a wide range, preferably from approx. 0.1 to 1.3 mm before coating, more preferably 0.3 to 0.7, and most preferably from 0.4 to 0.6 mm, these values being measured according to ISO 9073-1:1997-2. In this case, the measured surface area is 25 cm² at a pressure of 0.5 kPa. The density of preferred fibre non-woven fabrics lies within the range of 0.05 to 0.50 g/cm³, in particular 0.15 to 0.30 g/cm³.

Furthermore, the filters according to the invention incorporate a polymeric coating material which is applied to the support material.

After the hydrophobic support material has been coated with the polymeric coating material, the filter exhibits a critical surface wetting tension ranging from 50 to 80 dyn/cm, in particular 55 to 72 dyn/cm, preferably 55 to 69 dyn/cm. This value may be determined according to the method described in U.S. Pat. Nos. 5,445,736 and 4,880,548.

To achieve such a surface wetting tension, the polymeric coating agents incorporate hydrophilic groups, which are preferably groups which are ionically charged in water at pH 7.0. These groups include, among other things, groups that are anionically charged in water at pH 7.0, for example sulphonic acid, phosphonic acid and carboxy groups. Under the above conditions, cationically charged groups may also be present to achieve the required surface wetting tension. These cationic groups include, in particular, amino, N-pyrrolidone and guanidino groups. Moreover, the polymers may also incorporate neutral, polar groups such as polyethylene glycol units.

Accordingly, the polymeric coating agents may be obtained, for example, by polyreactions in which hydrophilic and hydrophobic monomers are used. The terms hydrophobic and hydrophilic are generally known in this specialist field and relate to the wettability of the polymers obtained from the monomers with water. Wettability with water is increased by polar groups which are present in the polymer after the polyreaction. Correspondingly, monomers are hydrophilic if they contain polar groups, e.g. hydroxyl, ether, carboxyl, carboxylate, amide, amine, pyrrolidine, pyrrolidone, lactam, sulphonate, phosphonate or guanidine groups, and a relatively low proportion of apolar groups, in particular hydrocarbon groups. The hydrophilicity of many monomers may be determined, for example, from the solubility of a homopolymer. If different monomers are required to produce the polymers, e.g. in the case of many polyesters, the hydrophilicity of the monomer is determined from the solubility of a polymer which, in addition to the monomer, also incorporates a suitable second monomer with an ethylene group. To determine the hydrophilicity of terephthalic acid, the latter is converted with glycol, for example. The hydrophilicity is obtained from the solubility of PET.

Generally speaking, a monomer is hydrophilic if the solubility of the homopolymer or a previously disclosed polymer is greater than or equal to 1 g/l, in particular 5 g/l, and more particularly 10 g/l.

Generally speaking, a monomer is hydrophobic if the solubility of the homopolymer or a previously disclosed polymer is less than 1 g/l, in particular less than or equal to 0.5 g/l, and more particularly less than or equal to 0.1 g/l.

It is known to the expert that the solubility of the polymers depends on the molecular weight. The previously disclosed solubility values are applicable for a molecular weight of 200,000 g/mol averaged over the weight. Here it is possible to determine this molecular weight by methods known to the expert, for example gel permeation chromatography. The temperature for determining this solubility is 20° C.

The previously disclosed polyreactions are generally well known and include, in particular, radical polymerizations, polyadditions and polycondensations.

The hydrophobicity of radically polymerisable monomers can be estimated on the basis of the miscibility or solubility of these monomers in water. Hydrophobic monomers are generally characterised by very limited miscibility in water, whereas hydrophilic monomers are readily miscible with water.

According to a particular embodiment of this invention, preferred hydrophobic, radically polymerisable monomers are characterised by a solubility in water less than or equal to 20 g/l, in particular 16 g/l and more particularly 10 g/l at 20° C. Compared to this, the solubility of preferred hydrophilic, radically polymerisable monomers at 20° C. is at least 50 g/l, preferably at least 100 g/l, and more preferably the hydrophilic monomers are miscible with water at 20° C. in any ratio.

The radically polymerisable, hydrophobic monomers include, among other things, vinyl ester such as vinyl acetate; alkenes such as ethylene, propylene, hexane-1, heptene-1, vinyl cyclohexane, 3,3-dimethyl-1-propene, 3-methyl-1-di-isobutylene, 4-methyl pentene-1; and alkyl(meth)acrylates which are derived from saturated alcohols, for example methyl acrylate, ethyl(meth)acrylate, propyl(meth)acrylate, n-butyl(meth)acrylate, tert.-butyl(meth)acrylate, the expression (meth)acrylates incorporating methacrylates and acrylates, as well as mixtures of both.

The radically polymerisable, hydrophilic monomers include, among other things, monomers with an acid group, for example vinylphosphonic acid, vinyl sulphonic acid, acrylic acid and methacrylic acid; monomers with a basic group, in particular vinyl pyridine, 3-vinyl pyridine, 2-methyl-5-vinyl pyridine, 3-ethyl-4-vinyl pyridine, 2,3-dimethyl-5-vinyl pyridine, N-vinyl pyrrolidone, 2-vinyl pyrrolidone, N-vinyl pyrrolidine and 3-vinyl pyrrolidine; as well as monomers with a polar group, such as 2-methacryl oxyethylphosphorylcholin, vinyl alcohol; vinyl alcohol can be obtained after polymerisation by saponifying vinyl esters.

Particularly preferred monomers exhibit at least one ionic group at pH 7.0. These include, among other things, the aforementioned monomers which exhibit at least one basic or one acid group.

The hydrophobic monomers which can be used in a polyaddition or polycondensation reaction include, among other things, alkene oxides such as butylenes oxide, hexylene oxide; monomers which are used to produce polyesters, polycarbonates and polyurethanes, such as isophorone diisocyanate, hexamethylene diisocyanate, hexane-1,6-diol and terephthalic acid.

The hydrophilic monomers which can be used in a polyaddition or polycondensation reaction include, among other things, ethylene oxide or glycol, which can, in particular, be used as polyethylene glycol.

The aforementioned hydrophilic and hydrophobic monomers can be used individually or as a mixture of two or more to obtain statistical copolymers, block copolymers and/or graft copolymers. Of these polymers, statistical copolymers are particularly preferred since they exhibit an essentially random incorporation of the different monomers, viewed across the polymer chain.

According to a particular embodiment of this invention, the mixtures for producing the polymeric coating material incorporate 1 to 40% by weight, preferably 4 to 25% by weight of hydrophilic monomers, and 99 to 60% by weight, and preferably 96 to 75% by weight of hydrophobic monomers without this imposing any limitation.

The polyreactions for producing the polymeric coating agents are of known in the art and are described, for example, in *Ullmann's Encyclopaedia of Industrial Chemistry, Fifth Edition on CDROM*, with further bibliographical references.

Furthermore, hydrophobic polymers may also be converted so that they exhibit the previously disclosed groups. This can be achieved, for example, by grafting reactions known in the art, where hydrophilic monomers are grafted on hydrophobic polymers. Moreover, hydrophobic polymers, such as polymethyl(meth)acrylates, can also be partially saponified to obtain polymers which exhibit carboxy groups.

The molecular weight of the polymers which are contained in the polymeric coating material may fluctuate within wide ranges. Generally, the mean weight of the molecular weight $M_w$ ranges from 10,000 to 200,000 g/mol, preferably 20,000 to 100,000 g/mol.

The polymers of the coating material preferably exhibit a polydispersity index $M_w/M_n$ ranging from 1 to 5, preferably 1.2 to 4, without this imposing any limitation.

The numerical mean of the molecular weight $M_n$ and the weight average of the molecular weight can be determined by gel permeation chromatography (GPC).

The polymeric coating material exhibits a solubility in water, at 20° C., less than or equal to 1 g/l, preferably less than or equal to 0.5 g/l. The low solubility of the polymer also relates, in particular, to the condition of the polymer before it is applied to the support material. This value can be determined gravimetrically.

The polymers of the coating material can be easily cleaned by precipitation from water from residual monomers and other by-products. For this purpose a solution of the polymers is simply added to a large quantity of water enabling the constituents soluble in water to be removed. The solvents in which the polymer can be dissolved include, among other things, alcohols, in particular ethanol; ketones, in particular acetone; and alkanes, in particular hexane.

After precipitation the polymers can be dried and incorporated once again in the organic solvent.

According to a particular embodiment of the invention, only a very small proportion of the coated support material can be extracted by water at 37° C. At a flow rate of 1 l/h, a maximum of 0.5% by weight, preferably a maximum of 0.3% by weight, related to the total weight of the coated filter, can be extracted within 1 hour. This proportion can be determined gravimetrically.

The low extractability of preferred coated filter materials may be reflected, among other things, in a low oxidation level. To determine the oxidation level a filter with 30 filter layers, at a surface density of approx. 60 g/m² and a filter area of approx. 50 cm², can be extracted with 250 ml of water for 2 hours at 37° C. 20 ml of the extracted solution can then be treated with 20 ml of a 0.01 N potassium permanganate solution in the presence of 1 ml of sulphuric acid, where the reaction mixture is heated for 3 minutes with reflux. An excess of potassium iodide can then be added at 20° C. The proportion of oxidisable compounds in the extract is determined by titrating the iodine formed with a 0.01 N sodium thiosulphate solution. The oxidation level is obtained from the blind sample as the volume difference of extract to water. Preferred coated filter materials are characterised by an oxidation level $\Delta O_x$ less than or equal to 3 ml, in particular less than or equal to 2 ml.

The surface density of the coated filters is generally slightly higher than the surface density of the fibre non-woven fabrics. Generally this value ranges from 16 to 240 g/m², in particular from 20 to 110 g/m², and more particularly from 26 to 70 g/m², without this imposing any limitation.

The support material and the polymeric coating material are preferably biocompatible, referring to the high compatibility of the materials.

Generally the polymeric coating agent covers at least 50%, preferably at least 90%, and more preferably at least 99% of the surface of the support material. This value can be determined by different methods known in the art, according to the combination of support material and coating agent. Here, calibration curves are normally produced for the relevant methods. These methods include, among other things, spectroscopic methods, such as the ESCA method, and optical methods where, for example, the coating material is dyed by the formation of complexes with iodine, whereas the support material is not dyed by iodine. The coverage of the surface can be determined by the proportion of the surface dyed by iodine.

The quantity of coating material which is applied to the support material depends both on the properties of the support material and on those of the coating material. Here, a critical surface wetting tension ranging from 50 to 80 dyn/cm must be achieved. Accordingly, this value may lie within a wide range. Generally, the filter incorporates 1 to 25% by weight of polymeric coating material and 99 to 75% by weight of support material.

According to a particular embodiment of the invention, the polymeric coating material may be extracted from the filter with one of the organic solvents. The extraction can, in particular, be carried out at temperatures slightly below the boiling point of the solvent concerned.

The filters according to the invention, for separating leukocytes from whole blood, can easily be produced by coating a hydrophobic support material with a solution which contains a polymeric coating material and a solvent, then removing the solvent from the support material provided with a polymeric coating agent.

The coating of the support material can be carried out by any known method, for example, immersion methods.

The proportion of solvent in the solution depends on the quantity of polymeric coating material applied to the support material. The solutions preferably contain 50 to 99.5% by weight, and more preferably 70 to 99% by weight, of solvent.

The filters according to this invention are generally used in devices for cleaning blood preparations. Such devices normally incorporate a container, for example a bag containing the blood to be cleaned, a housing divided by the filter into two chambers, and a further container in which the filtrate is trapped, these parts of the device being connected by hose pipes. The blood can be transferred from the first container via the filter to the second container by gravity alone, for example, or by means of a pump, preferably a peristaltic pump. Such devices are described, for example, in U.S. Pat. No. 5,445,736 and U.S. Pat. No. 5,162,102.

The filter located in the housing may incorporate one or more filter layers. According to a particular embodiment of the invention, the filters incorporate 15 to 50, preferably 20 to 40, filter layers.

The invention is explained in greater detail in the following examples and comparative examples, without the invention being limited to these examples.

Example 1

A statistical copolymer of vinyl acetate and vinyl pyrrolidone was produced by radical polymerisation, in which a vinyl acetate to vinyl pyrrolidone weight ratio of 7 was used.

For this purpose, the liquid reagents were cleaned by distillation in a nitrogen atmosphere. 98.5 g of vinyl acetate, 14 g of vinyl pyrrolidone and 0.59 g of azobis isobutyronitrile were added to 200 ml of acetone. The mixture obtained was agitated for 72 hours at approx. 54° C. in a nitrogen atmosphere. The polymer obtained was then extracted with 200 ml of hexane. The polymer was precipitated from the hexane solution by the addition of 1000 ml of water. The isolated polymer was dissolved in acetone and a statistical copolymer was obtained whose weight average of the molecular weight according to gel permeation chromatography was 56,611 g/mol and whose polydispersity index was 3.5, a styrene divinylbenzole polymer being used as the stationary phase and chloroform as the fluid phase.

The polymer thus obtained was cleaned several times by precipitation in water in order to remove monomer residues. For this purpose, the polymer was dissolved in acetone and added to water at room temperature. The precipitate was dried and again dissolved in acetone.

An acetonic solution was then produced which contained 4% by weight of polymer. A polybutylene terephthalate non-woven fabric was immersed in this solution, the fabric having a surface density of 50 g/m$^2$ and was produced from fibres with a diameter of 2 μm (available from Fresenius HemoCare Italia).

After immersion excess solution was dripped. The coated non-woven fabric was then dried using a conventional device (treatment rate 5 m/min at 95° C.). The surface density was 58.8 g/m$^2$.

30 layers of the coated non-woven fabric were inserted in a rectangular filter housing with a filter area of 50 cm$^2$. Approx. 500 ml of whole blood was filtered through the filter thus obtained by the force of gravity. The blood platelet concentrations before and after filtration were determined with an automatic analysis device (Coulter Gen-s; Beckman). The number of leukocytes was measured with a haemocytometer from Nageotte, this number being counted after filtration in a Burker chamber using a diluted solution (Leukoplate solution from Sobioda).

The results obtained are shown in Table 1.

Furthermore, the filter thus obtained was tested for extractable compounds, for which purpose 250 ml of distilled water was pumped for 2 hours through the filter with a peristaltic pump in a circuit, the temperature being 37° C. and the flow rate 1 l/h. The mixture thus obtained was tested for residues, 0.1% by weight of residues being established related to the weight of the filter before extraction treatment.

Furthermore, the extract obtained was tested for oxidisable substances, for which purpose 20 ml of the extracted solution was treated with 20 ml of a 0.01 N potassium permanganate solution in the presence of 1 ml of sulphuric acid, the reaction mixture being heated for 3 minutes with reflux. An excess of potassium iodide was then added at 20° C. The iodine formed from this was titrated with a 0.01 N sodium thiosulphate solution. The oxidation level was obtained by means of a blind sample as the extract to water volume difference. The oxidation level was 0.4 ml.

Example 2

Example 1 was essentially repeated, but here a vinyl acetate to vinyl pyrrolidone weight ratio of 12 was used instead of a ratio of 7.

A statistical copolymer was obtained whose weight average of the molecular weight, according to gel permeation chromatography, was 56,611 g/mol and whose polydispersity index was 3.5.

The surface density of the coated non-woven fabric was 60.2 g/m2.

The results of the whole blood filtration are also shown in Table 1.

The analysis for extractable compounds gave an oxidation level of 1.2 ml, where 0.3% by weight of residues were present in the extract related to the weight of the filter before treatment.

Example 3

Example 1 was essentially repeated, but here a vinyl acetate to vinyl pyrrolidone weight ratio of 4 was used instead of a weight ratio of 7. The surface density of the coated non-woven fabric was 59.9 g/m$^2$.

Comparative Example 1

Example 1 was essentially repeated, but here uncoated fabric from polybutylene terephthalate was used to filter whole blood. The results are also shown in Table 1.

TABLE 1

| | Detection rate of blood platelets [%] | Number of leukocytes in 500 ml of filtrate* [10$^6$] | |
|---|---|---|---|
| Example 1 | 80 ± 2 | 0.8 ± 0.2 | VA/VP 7P |
| Example 2 | 70 ± 5 | 0.5 ± 0.2 | VA/VP 12P |
| Example 3 | 78 ± 9 | 0.6 ± 0.4 | VA/VP 4P |
| Comparative example 1 | 0 | 0.1 ± 0.1 | uncoated |

*The number before filtration was approx. 3 * 10$^9$

The invention claimed is:

1. A filter for the separation of leukocytes from at least one of whole blood and blood preparations, the filter comprising:
   a hydrophobic support material; and
   a polymeric coating material on the hydrophobic support material, wherein the polymeric coating material comprises a copolymer of hydrophobic monomers and hydrophilic monomers;
   wherein a surface of the filter exhibits a critical surface wetting tension in the range of from 50 to 80 dyn/cm,
   wherein the hydrophobic monomer is vinyl acetate and the hydrophilic monomer is vinyl pyrrolidone, and
   wherein the filter retains leukocytes and exhibits a high permeability to blood platelets and erythrocytes.

2. The filter according to claim 1, wherein a maximum of 0.5% by weight of the filter can be extracted by water at 37° C.

3. The filter according to claim 2, wherein the copolymer contains 1 to 40% by weight of hydrophilic monomers and 99 to 60% by weight of hydrophobic monomers.

4. The filter according to claim 1, wherein the polymeric coating material includes ionic groups at a pH of 7.0.

5. The filter according to claim 1, wherein the polymeric coating material covers at least 90% of a surface of the hydrophobic support material.

6. The filter according to claim 1, wherein the copolymer is created by a radical polymerisation.

7. The filter according to claim 1, wherein the polymeric coating material exhibits a weight average of the molecular weight $M_w$ in the range of from 10,000 to 200,000 g/mol.

8. The filter according to claim 1, wherein the polymeric coating material exhibits a polydispersity index $M_w/M_n$ in the range of from 1 to 5.

9. The filter according to claim 1, wherein the polymeric coating material is selected from the group consisting of a statistical copolymer and a non-statistical copolymer wherein the copolymer is created by a polyaddition.

10. The filter according to claim 1, wherein the hydrophobic support material includes crystalline fibres.

11. The filter according to claim 10, wherein the crystalline fibres contain polyester.

12. The filter according to claim 11, wherein the crystalline fibres exhibit a diameter in the range of from 0.5 to 8 μm.

13. The filter according to claim 10, wherein the hydrophobic support material is a fibre non-woven fabric.

14. The filter according to claim 1, wherein the polymeric coating material comprises from 1 to 25% by weight of the filter.

15. The filter according to claim 1, wherein the filter exhibits a surface density in the range of from 20 to 110 g/m$^2$.

16. The filter according to claim 1, wherein the copolymer is a statistical, non-statistical, or grafted copolymer.

* * * * *